United States Patent
Bae et al.

(10) Patent No.: US 11,492,357 B2
(45) Date of Patent: Nov. 8, 2022

(54) THIENO[3,2-D]PYRIMIDINE DERIVATIVE COMPOUND HAVING INHIBITORY ACTIVITY FOR PROTEIN KINASE

(71) Applicant: Hanmi Pharm. Co., Ltd., Hwaseong-si (KR)

(72) Inventors: In Hwan Bae, Hwaseong-si (KR); Seung Hyun Jung, Hwaseong-si (KR); Young Gil Ahn, Hwaseong-si (KR); Kwee Hyun Suh, Hwaseong-si (KR)

(73) Assignee: Hanmi Pharm. Co., Ltd., Seoul (KR)

( * ) Notice: Subject to any disclaimer, the term of this patent is extended or adjusted under 35 U.S.C. 154(b) by 0 days.

(21) Appl. No.: 16/768,538

(22) PCT Filed: Nov. 29, 2018

(86) PCT No.: PCT/KR2018/014997
§ 371 (c)(1),
(2) Date: May 29, 2020

(87) PCT Pub. No.: WO2019/107987
PCT Pub. Date: Jun. 6, 2019

(65) Prior Publication Data
US 2020/0308188 A1    Oct. 1, 2020

Related U.S. Application Data

(60) Provisional application No. 62/592,679, filed on Nov. 30, 2017.

(51) Int. Cl.
*C07D 495/04*    (2006.01)

(52) U.S. Cl.
CPC .................. *C07D 495/04* (2013.01)

(58) Field of Classification Search
CPC ........................ C07D 495/04; A61K 31/519
USPC ........................................ 544/278; 514/260.1
See application file for complete search history.

(56) References Cited

U.S. PATENT DOCUMENTS

| 9,156,852 B2 * | 10/2015 | Bae .................. A61P 19/02 |
| 9,388,165 B2 | 7/2016 | Bae et al. |
| 10,112,954 B2 | 10/2018 | Jung et al. |
| 2004/0014756 A1 | 1/2004 | Michaelides et al. |

FOREIGN PATENT DOCUMENTS

| JP | 2013518098 A | 5/2013 |
| JP | 2015522607 A | 8/2015 |
| KR | 10-2013-0132396 A | 12/2013 |
| KR | 10-2014-0110066 A | 9/2014 |
| WO | 2011062372 A2 | 5/2011 |
| WO | 2013100632 A1 | 7/2013 |

OTHER PUBLICATIONS

International Search Report and Written Opinion for PCT/KR2018/014997, dated Feb. 29, 2019, 13 pages.

* cited by examiner

*Primary Examiner* — Jeffrey H Murray
(74) *Attorney, Agent, or Firm* — Armstrong Teasdale LLP

(57) ABSTRACT

The present invention relates to a compound, 4-amino-N-(1-((3-chloro-2-fluoro-4-hydroxyphenyl)amino)-6-methyl-isoquinolin-5-yl)thieno[3,2-d]pyrimidine-7-carboxamide, and pharmaceutically acceptable salts thereof having inhibitory activity for protein kinases.

9 Claims, No Drawings

THIENO[3,2-D]PYRIMIDINE DERIVATIVE COMPOUND HAVING INHIBITORY ACTIVITY FOR PROTEIN KINASE

CROSS-REFERENCE TO RELATED APPLICATIONS

This application is a U.S. National Phase Application of PCT/KR2018/014997, filed Nov. 29, 2018, which claims the benefit of priority to U.S. Provisional Application Ser. No. 62/592679 filed on Nov. 30, 2017, the contents of which are hereby expressly incorporated by reference in their entirety.

TECHNICAL FIELD

The present invention relates to a thieno[3,2-d]-pyrimidine compound, 4-amino-N-(1-((3-chloro-2-fluoro-4-hydroxyphenyl)amino)-6-methylisoquinolin-5-yl)thieno[3,2-d]pyrimidine-7-carboxamide, and pharmaceutically acceptable salts thereof having inhibitory activity for protein kinases, and a pharmaceutical composition comprising the same as an active ingredient for the treatment of diseases caused by abnormal cell growth.

BACKGROUND ART

A protein kinase is an enzyme which plays a key role in mediating signal transduction via phosphorylation of a hydroxyl group present in a tyrosine, serine or threonine residue, and, thus, is involved in the regulation of cell growth, differentiation, and proliferation.

As is well known, a balance between "on-states" and "off-states" of an intracellular signaling pathway is essential for maintenance of homeostasis of a cell. When a normal intracellular signaling pathway of, e.g., mostly continuation of "on-state" of intracellular signals is interrupted due to overexpression or mutation of a specific protein kinase, it may lead to an outbreak of various diseases such as cancer, inflammatory disease, metabolic disease and brain disease. It is estimated that human genome contains 518 protein kinases which constitute approximately 1.7% of all human genes [Manning et al., Science, 298, (2002), 1912]. The protein kinases can be divided into tyrosine protein kinases (90 or more types) and serine/threonine protein kinases. The tyrosine protein kinases can be divided into receptor tyrosine kinases including 58 distinct kinases which can be further categorized into 20 subtypes, and cytoplasmic/non-receptor tyrosine kinases including 32 distinct kinases which can be further categorized into 10 subtypes. A receptor tyrosine kinase has a kinase domain on the surface where it can bind a growth factor, and an active site where phosphorylation of a tyrosine residue takes place. Binding of a growth factor to the extracellular domain of the receptor may cause the receptor tyrosine kinase to form a polymer, which may result in autophosphorylation of specific tyrosine residues in the cytoplasmic domain. This may trigger, a cascade of events through phosphorylation of intracellular proteins that ultimately transmit the extracellular signal to the nucleus, thereby causing transcription and synthesis of various genes that may be involved in cell growth, differentiation, proliferation and the like.

Among the various cytoplasmic kinases, RAF is one of the kinases that participate in the linear Ras-RAF-MEK-ERK mitogen-activated protein kinase (MAPK) pathway initiated by a receptor protein kinase, which is activated by a growth factor [Solit, D. B. et al., Nature, 439, (2006), 358]. There are known three types of RAF isoforms, A-RAF, B-RAF and C-RAF (RAF-1) [Jansen H W, et al., EMBO J, 2, (1983), 1969; Marais R. et al., Cancer Surv, 27, (1996), 101]. Since abnormal activation in the MAPK pathway has been observed in approximately 30% of human cancer tissues and gene mutation of B-RAF and C-RAF showing aberrant activation has been confirmed in cancer tissues, it is generally accepted that RAF plays a very important role in the MAPK pathway of cancer tissues.

Accordingly, there have been suggested methods of using a compound having an inhibitory effect against abnormal activities of RAF kinases for treatment of cancer. Hence, a number of RAF and modified RAF kinase inhibitors are currently under development or being tested in ongoing clinical studies. Examples of such RAF kinase inhibitors include sorafenib (Nexavar®, Bayer) which is used for treatment of liver cancer, and vemurafenib (ZELBORAF®, PLX-4032, RG7204, Roche) which has been approved for treatment of melanoma. Other examples of RAF kinase inhibitors that are currently being tested in clinical trials include: regorafenib and RDEA119 by Bayer; RAF265 by Novartis; E3810 by Advan Chem; DCC2036 by Deciphera Pharma.; CKI27 by Chugai Pharma.; and RO-5126766 by Roche.

However, efficacy of such drugs has been questioned when they are administered over a duration of time despite their good initial performance, as drug resistance has been observed in some patients about 7 months after the initial administration of the drug.

It has been postulated that such degradation may be due to the drug resistance of B-RAF inhibitors, which is caused by abnormal activation of the MAPK pathway due to changes in RAF, activation of complementary signaling systems among different RAF isoforms, or activation of various receptor kinases other than MAPK as a result of activation of different pathways of Ras, a key protein used in the signal-transducing cascade which consists of K-Ras, N-Ras and H-Ras subtypes.

One of the signaling pathways that does not involve RAF kinases is C-FMS (cellular feline McDonough sarcoma), also known as colony-stimulating factor-1 receptor (CSF-1R), which is a member of the family of genes originally isolated from the Susan McDonough strain of feline sarcoma viruses. FMS is a receptor for macrophagecolony-stimulating factor (M-CSF) encoded by the C-FMS proto-oncogene, which belongs to a class III RTK along with Kit, Flt-3 and PDGFR. It has been reported that FMS tyrosine kinase is involved in cancer metastasis.

Another example is a receptor protein tyrosine kinase called discoidin domain receptor (DDR), which is a subfamily of receptor tyrosine kinases that possess an extracellular domain related to the lectin discoidin. In case of animals such as humans, there are two types of DDR proteins, DDR1 type and DDR2 type, which have similar amino acid sequences, but that are encoded by different genes. It has been reported that DDR proteins may be implicated in the process of cancer growth and metastasis. In addition, an upregulated expression of DDR has been observed in some tumor cells, along with a report that an upregulated expression of DDR raised expression of MMP1 and MMP-2 which are known to be implicated in cancer growth. Thus, it is believed that inhibition of such kinases can lead to a therapeutic effect against various types of cancer.

Compounds having improved protein kinase inhibitory activity are disclosed in International Publication Number WO 2013/100632.

DISCLOSURE OF INVENTION

Technical Problem

There is a continuing need in the art for a compound having inhibitory activity against RAF, FMS, and DDR1 and DDR2 kinases and that provides for improved treatment of various cancers including drug-resistant cancer, as compared with a conventional RAF kinase inhibitor.

Solution to Problem

Accordingly, the present invention provides a compound and a pharmaceutical composition comprising same having efficacious pharmacokinetic and pharmacodynamic properties for prevention or treatment of intractable cancer, including drug-resistant cancer, by inhibiting RAF (a key regulator of cell growth, differentiation and proliferation), FMS, and DDR1 and DDR2 kinases.

One embodiment of the present invention relates to a compound, 4-amino-N-(1-((3-chloro-2-fluoro-4-hydroxyphenyl)amino)-6-methylisoquinolin-5-yl)thieno[3,2-d]pyrimidine-7-carboxamide, of formula (I), or a pharmaceutically acceptable salt, or hydrate thereof:

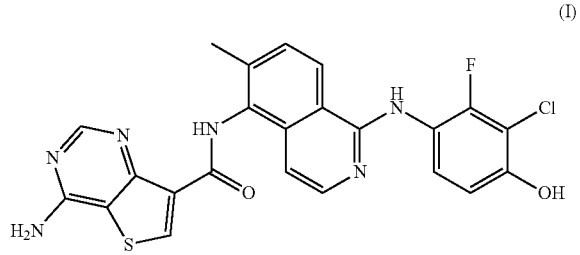 [SMILES: Cc1ccc2c(Nc3ccc(O)c(Cl)c3F)nccc2c1NC(=O)c1csc2c(N)ncnc12]

(I)

The term "salt or hydrate thereof", and variations thereof, as used herein in reference to the compound of formula (I), encompasses salts of the compound of formula (I), hydrates of the compound of formula (I), and hydrates of salts of the compound of formula (I).

In some embodiments, the compound of formula (I), or a pharmaceutically acceptable salt or hydrate thereof, has a purity of at least 95.0%.

In any of the various embodiments, the compound of formula (I), and pharmaceutically acceptable salts and hydrates thereof, have inhibitory activity against protein kinases.

In one embodiment, the inhibitory activity is against one or more of A-RAF, B-RAF, C-RAF, DDR1, DDR2 and FMS.

In one embodiment, formula (I) is a pan-RAF inhibitor. In such embodiments, the inhibitory activity is against A-RAF, B-RAF and C-RAF.

In another embodiment, the inhibitory activity is against FMS.

In still another embodiment, the activity is against DDR1 and DDR2 kinases.

Another aspect of the present invention also relates to a pharmaceutical composition comprising the compound of formula (I), or a pharmaceutically acceptable salt or hydrate thereof.

Another aspect of the present invention also relates to methods for prevention or treatment of a disease mediated by abnormal activation of one or more protein kinases, the method comprising administering any of the compounds or compositions comprising said compounds of the present invention to a mammal in need thereof.

Advantageous Effects of Invention

The inventive compound, 4-amino-N-(1-((3-chloro-2-fluoro-4-hydroxyphenyl)amino)-6-methylisoquinolin-5-yl)thieno[3,2-d]pyrimidine-7-carboxamide having inhibitory activity for protein kinases, can effectively inhibit various protein kinases including RAF, and thus can be used, singly or in combination, for prevention and treatment of diseases associated with aberrant cell growth which are caused by mutation or overexpression of RAS protein or overactivation of its associated protein kinases.

MODE FOR THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety.

The present disclosure relates to a compound 4-amino-N-(1-((3-chloro-2-fluoro-4-hydroxyphenyl)amino)-6-methylisoquinolin-5-yl)thieno[3,2-d]pyrimidine-7-carboxamide of formula (I) or a pharmaceutically acceptable salt or hydrate thereof:

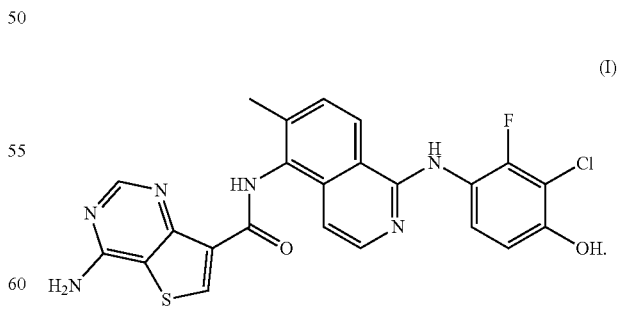

(I)

The compounds of the present disclosure have inhibitory activity against protein kinases. In one embodiment, the compounds are RAF inhibitors having inhibitory activity against at least one of the A-RAF, B-RAF and C-RAF isoforms. In one embodiment, the compounds are pan-RAF inhibitors having inhibitory activity against more than one of the A-RAF, B-RAF and C-RAF isoforms. In another embodiment, the inhibitory activity is against FMS. In another embodiment, the activity is against DDR1 and DDR2 kinases. In another embodiment, the activity is pan-RAF, is against DDR1 and DDR2 kinases, and is against FMS.

In some embodiments, the compound of formula (I), and pharmaceutically acceptable salts and hydrates thereof of the present invention are in solid form.

In some embodiments, the compound of formula (I), and pharmaceutically acceptable salts and hydrates thereof of the present invention are in solution in a pharmaceutical carrier. In some such embodiments, the concentration of formula (I) in solution is at least 0.01 mg/mL, at least 0.05 mg/mL, at least 0.1 mg/mL, at least 0.5 mg/mL, at least 1 mg/mL, at least 2 mg/mL, at least 3 mg/mL, at least 4 mg/mL or at least 5 mg/mL.

In any of the various embodiments, the purity of the compound of formula (I), or a pharmaceutically acceptable salt or hydrate thereof, is at least 95%, at least 96%, at least 97%, at least 98%, at least 98.5%, at least 99% or at least 99.5% as measured by HPLC. In any of the various embodiments, the assay of the compound of formula (I), or a pharmaceutically acceptable salt or hydrate thereof, is at least 95%, at least 96%, at least 97%, at least 98%, at least 98.5%, at least 99% or at least 99.5% as measured by HPLC.

The compound of the present invention may also form a pharmaceutically acceptable salt. Such salt may be a pharmaceutically acceptable nontoxic acid addition salt containing anion, but not limited thereto. For example, the salt may include acid addition salts formed by inorganic acids such as hydrochloric acid, sulfuric acid, nitric acid, phosphoric acid, hydrobromic acid, hydriodic acid, and others; organic carbonic acids such as tartaric acid, formic acid, citric acid, acetic acid, trichloroacetic acid, trifluoroacetic acid, gluconic acid, benzoic acid, lactic acid, fumaric acid, maleic acid, and others; and sulfonic acids such as methanesulfonic acid, benzenesulfonic acid, p-toluenesulfonic acid, naphthalensulfonic acid, and others. In a specific embodiment, the acid addition salt is one formed by sulfuric acid, methanesulfonic acid or a hydro-halogenic acid (e.g., hydrochloric acid). In one embodiment, the formula (I) salt is the bis-hydrochloride salt.

In addition, hydrates of the compound of formula (I) are encompassed within the scope of the present invention.

The compound of the present invention may be obtained via General Scheme 1 by using intermediates obtained in General Scheme 1 shown below, or starting materials or intermediates which are commercially available, respectively. Further, mass analysis of the obtained 4-amino-N-(1-((3-chloro-2-fluoro-4-hydroxyphenyl)amino)-6-methylisoquinolin-5-yl)thieno[3,2-d]pyrimidine-7-carboxamide may be performed by using MicroMass ZQ™ (Waters).

The pharmaceutical composition comprising, as an active ingredient, 4-amino-N-(1-((3-chloro-2-fluoro-4-hydroxyphenyl)amino)-6-methylisoquinolin-5-yl)thieno[3,2-d]pyrimidine-7-carboxamide or salts or hydrates thereof may be used for prevention or treatment of abnormal cell growth diseases caused by abnormal activation of one or more protein kinases.

In addition, the present invention relates to a method for preventing or treating a disease mediated by abnormal activation of one or more protein kinases, which method comprises administering the inventive compound to a subject in need thereof. For example, the subject is a mammal.

Examples of the protein kinases include ALK, AMPK, Aurora A, Aurora B, Aurora C, Axl, Blk, Bmx, BTK, CaMK, CDK2/cyclinE, CDK5/p25, CHK1, CK2, A-RAF, B-RAF, C-RAF, DDR1, DDR2, DMPK, EGFR1, Her2, Her4, EphA1, EphB1, FAK, FGFR2, FGFR3, FGFR4, Flt-1, Flt-3, Flt-4, FMS (CSF-1), Fyn, GSK3 beta, HIPK1, IKK beta, IGFR-1R, IR, Itk, JAK2, JAK3, KDR, Kit, Lck, Lyn, MAPK1, MAPKAP-K2, MEK1, Met, MKK6, MLCK, NEK2, p70S6K, PAK2, PDGFR alpha, PDGFR beta, PDK1, Pim-1, PKA, PKB alpha, PKC alpha, Plk1, Ret, ROCK-I, Rsk1, SAPK 2a, SGK, Src, Syk, Tie-2, Tec, Trk or ZAP-70. In some embodiments, the one or more protein kinases include one or more of A-RAF, B-RAF, C-RAF, DDR1, DDR2 and FMS. In some embodiments, the one or more protein kinases include one or more of A-RAF, B-RAF and C-RAF. In some embodiments, the one or more protein kinases include DDR1 and/or DDR2. In some embodiments, the protein kinase is FMS. The pharmaceutical composition in accordance with the present invention has inhibitory activity against the above kinases.

Examples of the abnormal cell growth diseases caused by abnormal activation of one or more protein kinases in which the inventive pharmaceutical composition is effective against include gastric cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophagus cancer, thyroid cancer, parathyroid cancer, renal cancer, sarcoma, prostate cancer, urethral cancer, bladder cancer, blood cancer, lymphoma, fibroadenoma, inflammation, diabetes, obesity, psoriasis, rheumatoid arthritis, hemangioma, acute and chronic kidney disease, coronary restenosis, autoimmune diseases, asthma, neurodegenerative diseases, acute infection and ocular diseases caused by angiogenesis. In some embodiments, the cancer is melanoma or liver cancer.

Pharmaceutical compositions of the present disclosure may comprise a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogens, cell differentiation/proliferation/survival inhibitors, apoptosis inhibitors, inflammation inhibitors and P-glycoprotein inhibitors. In case where the inventive pharmaceutical composition is developed into a formulation, it may be used in combination with said drug or developed into a combined formulation with said drug.

In some embodiments, the drug is a cell signal transduction inhibitor. In some such aspects the cell signal transduction inhibitor is a MEK inhibitor. Non-limiting examples of MEK inhibitor drugs include the following. COTELLIC® (cobimetinib); (GDC-0973; Genentech); [3,4-difluoro-2-(2-fluoro-4-iodoanilino)phenyl]-[3-hydroxy-3-[(2S)-piperidin-2-yl]azetidin-1-yl]methanone; CAS#934660-93-2. GDC-0623 (Genentech); 5-((2-fluoro-4-iodophenyl)amino)-N-(2-hydroxyethoxy)imidazo[1,5-A]pyridine-6-carb oxamide; CAS#1168091-68-6. RO4987655 (Hoffman-La Roche); CH4987655; 3,4-difluoro-2-(2-fluoro-4-iodoanilino)-N-(2-hydroxyethoxy)-5-[(3-oxooxazinan-2-yl) methyl]benzamide; CAS#874101-00-5. RO5126766 (Hoffman-La Roche); 3-[[2-[(Methylaminosulfonyl)amino]-3-fluoropyridin-4-yl]methyl]-4-methyl-7-[(pyrimidin-2-yl)oxy]-2H-1-benzopyran-2-one; CAS#946128-88-7. Trametinib (GlaxoSmithKline); GSK1120212; N-[3-[3-cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]-acetamide; CAS#871700-17-3. Pimasertib (Array BioPharma and AstraZeneca); AS-703026; Merck. Selumetinib; AZD6244; 6-(4-bromo-2-chloroanilino)-7-fluoro-N-(2-hydroxyethoxy)-3-methylbenzimidazole-5-carboxamide; CAS#606143-52-6. Refametinib (Bayer); RDEA119; Bay 86-9766; N-[3,4-difluoro-2-(2-fluoro-4-iodoanilino)-6-methoxyphenyl]-1-[(2S)-2,3-dihydroxyprop yl]cyclopropane-1-sulfonamide; CAS#923032-37-5. PD184352 (Pfizer); CI-1040; (2-Chloro-4-iodophenylamino)-N-cyclopropylmethoxy-3,4-difluorobenzamide; CAS#212631-79-3. Binimetinib (Array BioPharma and Novartis); MEK162; 5-((4-bromo-2-fluorophenyl)amino)-4-fluoro-N-(2-hydroxyethoxy)-1-methyl-1H-benz o[d]imidazole-6-carboxamide; CAS#606143-89-9. PD0325901 (Pfizer); N-[(2R)-2,3-Dihydroxypropoxy]-3,4-difluoro-2-[(2-fluoro-4-iodophenyl)amino]-benzamide; CAS#391210-10-9. AZD8330 (AstraZeneca); 2-(2-fluoro-4-iodophenylamino)-N-(2-hydroxyethoxy)-1,5-dimethyl-6-oxo-1,6-dihydropyridine-3-carboxamide; CAS#869357-68-6. TAK-733 (Millennium Pharmaceutical and Takeda Pharmaceutical Company); (R)-3-(2,3-dihydroxypropyl)-6-fluoro-5-(2-fluoro-4-iodophenylamino)-8-methylpyrido[2,3-d]pyrimidine-4,7(3H,8H)-dione; CAS#1035555-63-5. WX-554 (Wilex, AG). HL085 (Binjiang Pharma). Regorafenib (Bayer); 4-(4-(3-(4-Chloro-3-(trifluoromethyl)phenyl)ureido)-3-fluorophenoxy)-N-methylpicolinamide; CAS#755037-03-7. RAF265 (Novartis); CHIR-265; 1-methyl-5-[2-[5-(trifluoromethyl)-1H-imidazol-2-yl]pyridin-4-yl]oxy-N-[4-(trifluoro methyl)phenyl]benzimidazol-2-amine; CAS#927880-90-8. Lucitanib (Advan Chem); E3810; 6-((7-((1-aminocyclopropyl)methoxy)-6-methoxyquinolin-4-yl)oxy)-N-methyl-1-naphthamide; CAS#1058137-23-7. Rebastanib (Deciphera Pharm); DCC2036; 4-[4-[[[[3-(1,1-dimethylethyl)-1-(6-quinolinyl)-1H-pyrazol-5-yl]amino]carbonyl]amino]-3-fluorophenoxy]-N-methyl-2-pyridinecarboxamide; CAS#1020172-07-9. CK-127 (Chugai Pharma); RG7304; (E)-5-(2-benzylidene-1-methylhydrazinyl)pyridazin-3(2H)-one; CAS#213406-50-9. In some embodiments, the drug is cobimetinib.

The inventive pharmaceutical composition may comprise conventional pharmaceutically acceptable excipients including carriers, diluents, adjuvants, additives and vehicles. The pharmaceutical composition may be formulated in accordance with conventional methods, and may be prepared in the form of oral formulations such as a tablet, pill, powder, capsule, syrup, an emulsion, a microemulsion and others or parenteral formulations such as intramuscular, intravenous or subcutaneous administration.

When the pharmaceutical composition according to the present invention is prepared as a formulation for oral administration, the carrier to be used may include, for instance and without limitation, cellulose, calcium silicate, corn starch, lactose, sucrose, dextrose, calcium phosphate, stearic acid, magnesium stearate, calcium stearate, gelatin, talc, surfactant, suspending agents, emulsifying agents, diluents, and combinations thereof. Additionally, when the pharmaceutical composition is prepared as a formulation for oral administration, the diluents to be used may include, for instance and without limitation, lactose, mannitol, saccharide, microcrystalline cellulose, cellulose derivative, corn starch, and combinations thereof. Formulations for oral administration may also include, for instance and without limitation, polymers (for instance hydrophilic polymers such as polyvinylpyrrolidone), antioxidants, preservatives, wetting agents, lubricating agents, glidants, processing aids, granulating agents, dispersing agents, colorants, and flavoring agents.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed and optionally are formulated so as to provide slow or controlled release of the active ingredient therefrom.

When the pharmaceutical composition according to the present invention is prepared as a formulation for injections, the carrier to be used may include, for instance and without limitation, water, saline, an aqueous glucose solution, an aqueous sugar-like solution, alcohols, glycols (e.g., polyethylene glycol 400), ethers, oils, fatty acids, fatty acid esters, glycerides, surfactants, suspending agents, emulsifying agents, and combinations thereof.

EXAMPLES

Example 1: Preparation of Compound Formula (I)

Compound formula (I) may be prepared according to steps 1 to 4 as follows.

The following abbreviations are used in Preparation Examples, Preparation Methods and Examples below:

| Abbreviation | Definition |
|---|---|
| Fe | Iron, powder |
| CDMT | 4-Chloro-2,6-dimethoxy-1,3,5-triazine |
| NMM | 4-Methylmorpholine |
| TEA | Triethylamine |
| $CHCl_3$ | Chloroform |
| IPA | Isopropyl alcohol |
| EA | Ethyl acetate |
| Hex | n-Hexane |
| EtOH | Ethyl alcohol |
| MeOH | Methyl alcohol |
| DMF | N,N-dimethylformamide |
| PW | Purified water |
| conc. HCl | 35% Hydrochloric acid in water |
| $MgSO_4$ | Magnesium sulfate |
| $NaHCO_3$ | Sodium bicarbonate |
| Brine | Sodium chloride in Water |
| RBF | Round-bottom flask |
| NMR | Nuclear Magnetic Resonance |

The compound of formula (I) of the present invention may be prepared via General Scheme 1 by using intermediates obtained in General Scheme 1 shown below, or starting materials or intermediates which are commercially available, respectively.

General Scheme 1

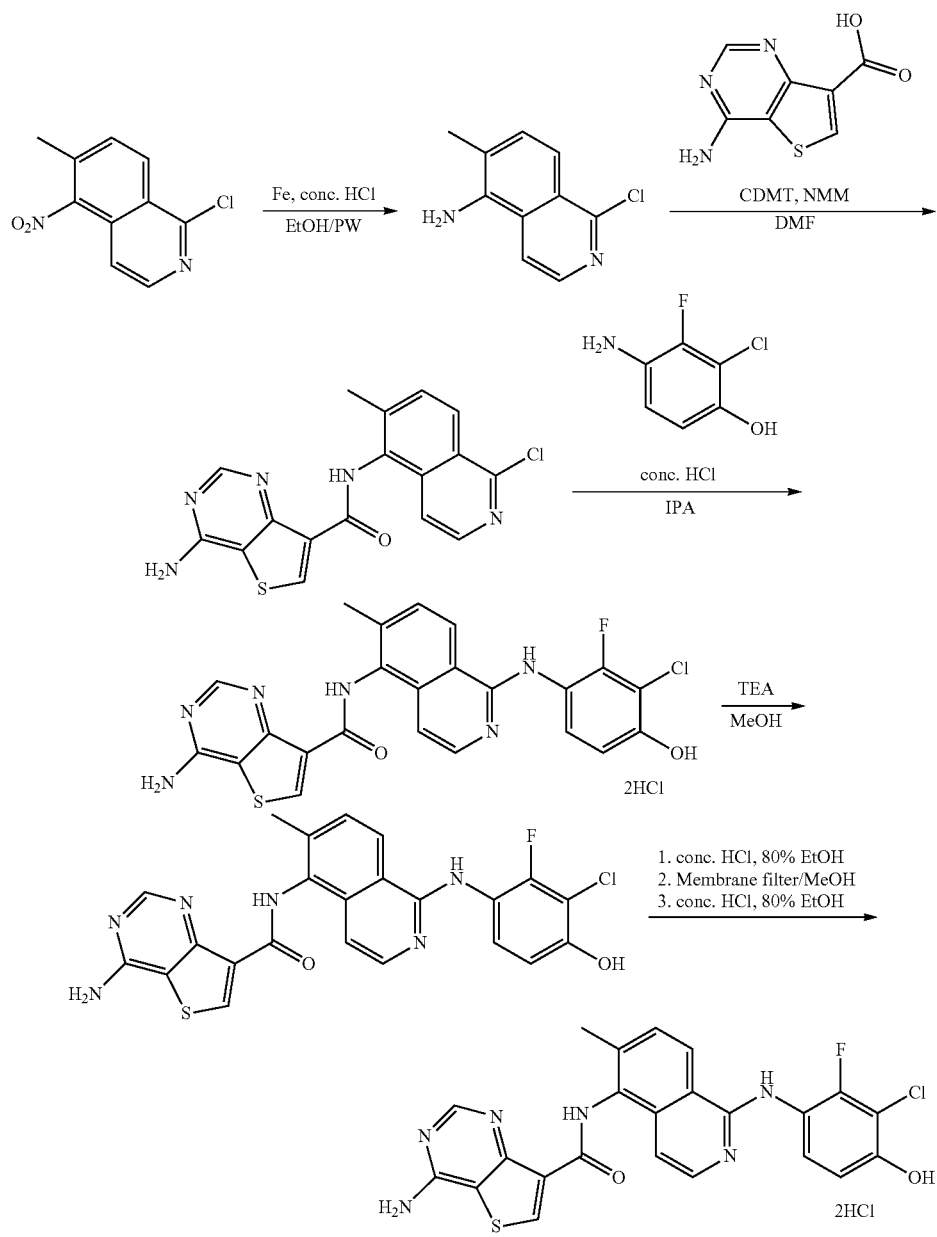

The above reaction processes are exemplified in the following stepwise reactions.

Step 1: Preparation of 1-chloro-6-methylisoquinolin-5-amine

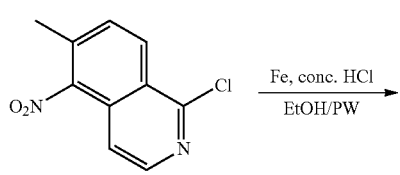

-continued

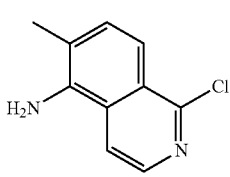

15.1 g of iron powder (0.27 mol, 3.0 eq.) and 0.3 mL concentrated HCl (0.005 mol, 0.05 eq.) were added to a 300 mL 1:1 mixed solution of ethyl alcohol/purified water (15 v/w). The reaction mixture was heated up to 90° C., followed by stirring for 1 hour. 20.0 g of 1-chloro-6-methyl-5-nitroisoquinoline (0.09 mol, 1.0 eq.) was added to the reaction mixture and stirred at reflux for 5 hours. The reaction mixture was filtered through a pad of Celite® (diatomaceous earth) under reduced pressure, and washed with a 100 mL 4:1 mixed solution of chloroform/isopropyl alcohol (5 v/w). The filtrate was evaporated under reduced pressure, and the residue was dissolved in a 200 mL 4:1 mixed solution of chloroform/isopropyl alcohol (10 v/w). The organic layer was washed with 100 mL aqueous solution of sodium bicarbonate (5 v/w), and 100 mL brine (5 v/w). The obtained organic layer was dried over anhydrous magnesium sulfate and concentrated under reduced pressure. The concentrated solid was dried under oven at 45° C. for 12 hours to obtain the desired compound as a brown solid (14.3 g, 83%).

$^1$H-NMR spectrum (300 MHz, DMSO-$d_6$) δ 8.12 (m, 2H), 7.48 (q, 2H), 5.87 (s, 2H), 2.28 (s, 3H).

Step 2: Preparation of 4-amino-N-(1-chloro-6-methylisoquinolin-5-yl)thieno[3,2-d]pyrimidine-7-carboxamide

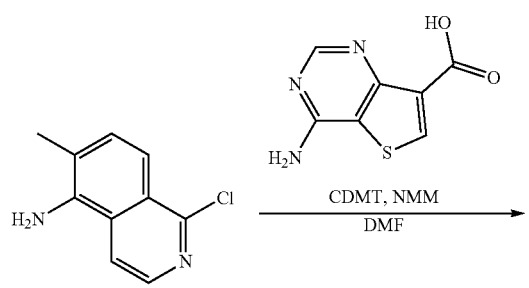

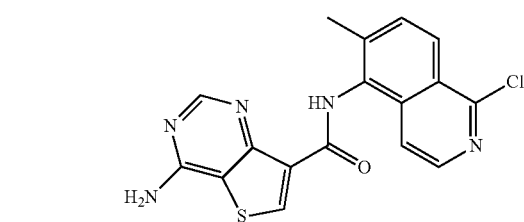

The 4-aminothieno[3,2-d]pyrimidine-7-carboxylic acid 28.5 g (0.15 mol, 1.0 eq.) was dissolved in 300 mL N,N-Dimethylformamide (10 v/w), with subsequent addition of 25.7 g of 4-chloro-2,6-dimethoxy-1,3,5-triazine (0.15 mol, 1.0 eq.) and 16.1 mL 4-methylmorpholine (0.15 mol, 1.0 eq.) at 20-30° C., followed by stirring for 20 minutes. 28.1 g of 1-chloro-6-methylisoquinolin-5-amine (0.15 mol, 1.0 eq.) was then added to the reaction mixture at 20-30° C., followed by stirring for 12 hours. To the reaction mixture was added 300 mL purified water (10 v/w) and the reaction mixture was stirred for 1 hour. The reaction mixture was filtered under reduced pressure, and washed with 90 mL purified water (3 v/w). The obtained solid was dried under oven at 45° C. for 12 hours to obtain the desired compound as a brown solid (33.2 g, 61%).

$^1$H-NMR spectrum (300 MHz, DMSO-$d_6$) δ 11.69 (s, 1H), 8.95 (s, 1H), 8.65 (s, 1H), 8.37 (m, 2H), 7.95 (s, 2H), 7.88 (m, 2H), 2.49 (s, 3H).

Step 3: Preparation of 4-amino-N-(1-((3-chloro-2-fluoro-4-hydroxyphenyl)amino)-6-methyliso quinolin-5-yl)thieno[3,2-d]pyrimidine-7-carboxamide dihydrochloride

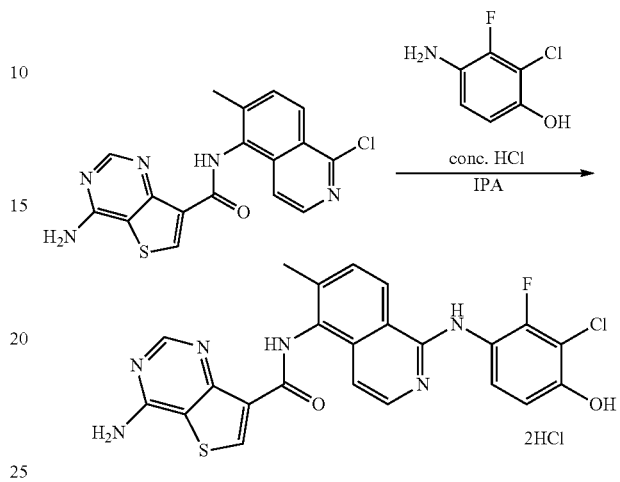

20 g of 4-amino-N-(1-chloro-6-methylisoquinolin-5-yl) thieno[3,2-d]pyrimidine-7-carboxamide (54.1 mmol, 1.0 eq.) and 17.4 g of 4-amino-2-chloro-3-fluorophenol (108.2 mmol, 2.0 eq.) were added to a sealed tube and 200 mL isopropyl alcohol (10 v/w) and 13.5 mL concentrated HCl (162.2 mmol, 3.0 eq.) were added to the reaction mixture at 20-25° C. The reaction mixture was heated up to 130° C., followed by stirring for 12 hours. The reaction solution was cooled to 20-30° C. The solid was filtered under reduced pressure, followed by washing with 50 mL isopropyl alcohol 100 mL (5 v/w) to obtain the desired compound as a dark brown solid (23.5 g, 77%).

Step 4: Preparation of 4-amino-N-(1-((3-chloro-2-fluoro-4-hydroxyphenyl)amino)-6-methyliso quinolin-5-yl)thieno[3,2-d]pyrimidine-7-carboxamide

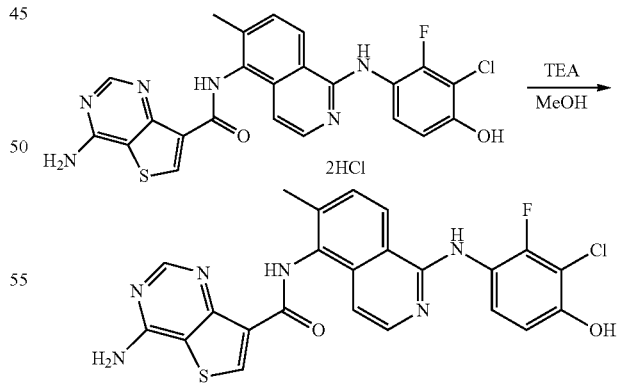

23.5 g of 4-amino-N-(1-((3-chloro-2-fluoro-4-hydroxyphenyl)amino)-6-methylisoquinolin-5-yl)thieno[3,2-d]pyrimidine-7-carboxamide dihydrochloride (41.4 mmol, 1.0 eq.) was added to a 1 L round-bottom flask and 470 mL methyl alcohol (20 v/w) was added. 12.7 mL triethylamine (91.0 mmol, 2.2 eq.) was added to the reaction mixture at 20-25° C., followed by stirring for 2 hours. The solid was filtered under reduced pressure, followed by washing with 100 mL methyl alcohol (5 v/w). The filtered solid was dried under oven at 45° C. for 12 hours to obtain the desired compound as brown solid (11.7 g, 57%).

$^1$H-NMR spectrum (300 MHz, DMSO-d$_6$) δ 11.53 (s, 1H), 10.48 (br, 1H), 8.97 (s, 1H), 8.92 (d, 1H), 8.50 (s, 1H), 8.32 (d, 1H), 7.94 (s, 2H), 7.79 (d, 1H), 7.55 (d, 1H), 7.20 (t, 1H), 7.04 (d, 1H), 6.82 (d, 1H), 2.41 (s, 3H).

Example 2: Preparation of Compound Formula (I) Bis-Hydrochloride Salt

Step 1: Preparation of 4-amino-N-(1-((3-chloro-2-fluoro-4-hydroxyphenyl)amino)-6-methylisoquinolin-5-yl)thieno[3,2-d]pyrimidine-7-carboxamide dihydrochloride

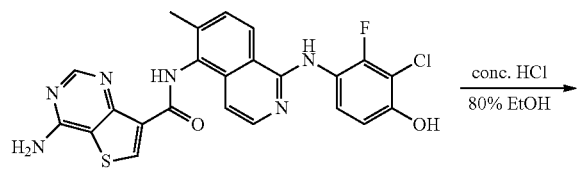

conc. HCl
80% EtOH

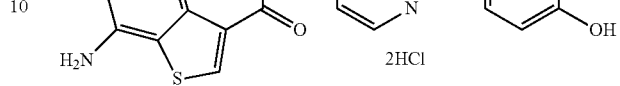

2HCl 11.7 g of 4-amino-N-(1-((3-chloro-2-fluoro-4-hydroxyphenyl)amino)-6-methylisoquinolin-5-yl)thieno[3,2-d]pyrimidine-7-carboxamide (23.6 mmol, 1.0 eq.) was added to a 500 mL round-bottom flask and 240 mL of 80% ethyl alcohol (20 v/w) was added, followed by the addition of 5.9 mL of concentrated HCl (70.9 mmol, 3.0 eq.) to the reaction mixture at 20-25° C. The reaction mixture was heated up to 90° C., followed by stirring for 2 hours. The reaction solution was cooled to 20-30° C. The solid was filtered under reduced pressure, followed by washing with 58.5 mL ethyl alcohol (5 v/w). The filtered solid was dried in an oven at 45° C. for 12 hours to obtain the desired compound as brown solid (10.9 g, 81%).

Step 2: Refinement of 4-amino-N-(1-((3-chloro-2-fluoro-4-hydroxyphenyl)amino)-6-methyliso quinolin-5-yl)thieno[3,2-d]pyrimidine-7-carboxamide dihydrochloride

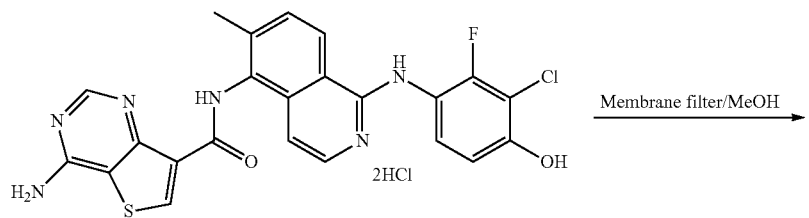

Membrane filter/MeOH

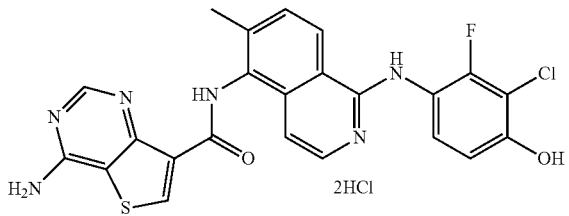

2HCl 10.9 g of 4-amino-N-(1-((3-chloro-2-fluoro-4-hydroxyphenyl)amino)-6-methylisoquinolin-5-yl)thieno[3,2-d]pyrimidine-7-carboxamide dihydrochloride was added to a 3 L round-bottom flask and 2 L of methyl alcohol (200 v/w) was added at 20-25° C. The reaction mixture was heated up to 50° C., followed by stirring for 30 min. The reaction mixture was cooled to 20-30° C. 1.1 g of activated carbon was added, followed by stirring for 3 hours. The reaction mixture was filtered through a pad of Celite under reduced pressure, followed by washing with 100 mL of methyl alcohol (10 v/w). The filtrate was filtered (using membrane filter paper) under reduced pressure, followed by washing with 100 mL of methyl alcohol (10 v/w). The filtrate was evaporated under reduced pressure. To the residue was added methyl alcohol (200 mL), followed by stirring for 2 hours. The solid was filtered under reduced pressure, followed by washing with 50 mL of methyl alcohol (5 v/w). The filtered solid was dried in an oven at 45° C. for 12 hours to obtain the desired compound as a pale brown solid (7.7 g, 71%).

Step 3: Refinement of 4-amino-N-(1-((3-chloro-2-fluoro-4-hydroxyphenyl)amino)-6-methyliso quinolin-5-yl)thieno[3,2-d]pyrimidine-7-carboxamide dihydrochloride

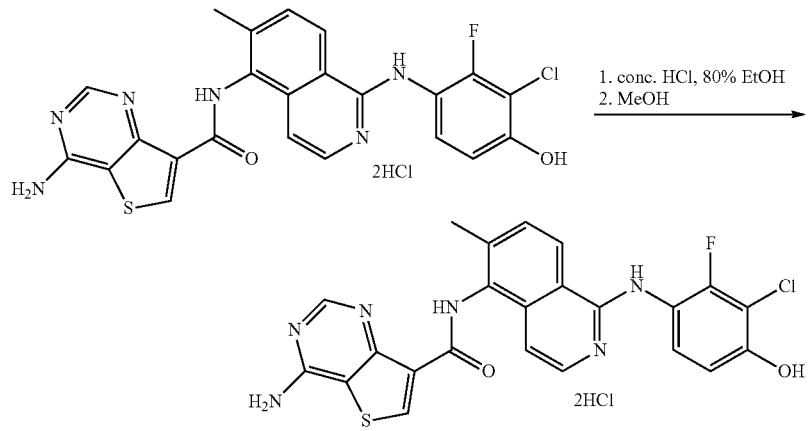

7.7 g of 4-amino-N-(1-((3-chloro-2-fluoro-4-hydroxyphenyl)amino)-6-methylisoquinolin-5-yl)thieno[3,2-d]pyrimidine-7-carboxamide dihydrochloride (13.6 mmol, 1.0 eq.) was added to a 250 mL round-bottom flask and 150 mL of 80% ethyl alcohol (20 v/w) and 2.3 mL of concentrated HCl (27.1 mmol, 2.0 eq.) were added to the reaction mixture at 20-25° C. The reaction mixture was heated up to 90° C., followed by stirring for 1 hour. The reaction solution was cooled to 20-30° C. The solid was filtered under reduced pressure, followed by washing with 38.5 mL of ethyl alcohol (5 v/w). To the resulting solid was added 385 mL of methyl alcohol (50 v/w). The reaction mixture was heated up to 40° C., followed by stirring for 3 hours. The solid was filtered under reduced pressure, followed by washing with 38.5 mL of methyl alcohol (5 v/w). The filtered solid was dried at 45° C. for 12 hours. The solid compound was then dried at 25° C., 90% RH for 12 hours. The hygroscopic solid was then dried at room temperature for 6 hours to obtain the desired compound as an off-white powder (4.8 g, 62%).
Purity: 97.0% by HPLC
Assay: 96.8% by HPLC
Moisture: 4.7%

1H-NMR spectrum (300 MHz, DMSO-d6) δ 11.60 (s, 1H), 11.42 (s, 1H), 9.47 (s, 1H), 8.88 (d, 1H), 8.62 (s, 1H), 7.88 (d, 1H), 7.56 (d, 1H), 7.42 (t, 1H), 7.32 (d, 1H), 7.10 (d, 1H), 2.50 (s, 3H).

Experimental Example 3: Evaluation of RAF Kinase Activity

Formula (I) bis-hydrochloride salt prepared in Example 2 (hereinafter referred to as "Compound•2HCl") was tested for inhibitory activity against three subtypes of RAF, i.e., RAF1 (C-RAF)$^{Y340D/Y341}$D, B-RAF wild type and B-RAF$^{V600E}$ using Kinase Profiling Service (Thermo Fisher Scientific, previously Invitrogen, U.S.A) according to the manufacturer's instructions. The levels of enzymatic inhibition of the compound were calculated as percent inhibition at various concentrations. Based on percent inhibition, dose-response curves were plotted using GraphPad Prism software. The $IC_{50}$ values of Compound•2HCl against C-RAFY$^{Y340D/Y341D}$, B-RAF$^{WT}$ and B-RAF$^{V600E}$ are listed in Table 1 where ZELBORAF® (vemurafenib, PLX-4032, Roche) was used as a control.

TABLE 1

| Example | B-RAF$^{WT}$ ($IC_{50}$, nM) | B-RAF$^{V600E}$ ($IC_{50}$, nM) | C-RAF$^{Y340D/Y341D}$ ($IC_{50}$, nM) |
|---|---|---|---|
| Control | 111 | 107 | 138 |
| Compound•2HCl | 392 | 30 | 21 |

Experimental Example 4: Evaluation of Inhibition on Cell Growth of N-RAS$^{Q61K}$ Mutant Cell Line SK-MEL-30 (Human Melanoma Cells)

The inventive compound was tested for inhibitory activities on proliferation aberrant cells as follows.
N-RAS$^{Q61K}$ mutant SK-MEL-30 melanoma cell line (ACC-151) was obtained from DSMZ (Deutsche Sammlung von Mikroorganismen und Zellkulturen GmbH, Germany). SK-MEL30 cells express wildtype B-RAF and mutant N-RAS (Q61K). SK-MEL-30 cells were incubated in a RPMI medium supplemented with 10% FBS and 1% penicillin/streptomycin (Gibco BRL) under 37° C., 5% CO2 and 95% air. Cells were seeded in 96-well plates at a density of 5,000 cells/well, and cultured for 18 hours or more. Then cells were treated with 0.1-10 μM (1/10 serial dilution) of test compounds, and incubated for 72 hours.

To evaluate cell viabilities, SK-MEL-30 cell lines were fixed with 10% TCA (trichloroacetic acid), stained with SRB (sulforhodamine B), and the absorbance was measured at 540 nm. Then, $GI_{50}$, i.e., the concentration of drug to cause 50% reduction in proliferation of cancer cells, was calculated therefrom. The growth rates of cancer cells were calculated by Equation 1 or 2.

[(Ti-Tz)/(C-Tz)]×100 (for Ti≧Tz)   Equation 1

[(Ti-Tz)/Tz]×100 (for Ti<Tz)   Equation 2

In Equation 1 and 2, 'Tz' refers to the density of untreated cells, which is the absorbance in 0% cell growth groups. 'C' refers to the density of cells cultured by adding only medium, and 'Ti' refers to the density of cells treated with test compounds.

$GI_{50}$ value is the concentration of a test compound when the value of Equation 1 is 50, which indicates the concentration of the test compound needed to reduce the growth of cancer cells to 50%. On each measurement, test compounds were compared with a vemurafenib (PLX-4032) control. The $GI_{50}$ values of each compound were measured and are shown in Table 2.

TABLE 2

| Example | SK-MEL-30 ($GI_{50}$, nM) |
|---|---|
| Control | >10,000 |
| Compound·2HCl | 231 |

As evidenced above, the inventive compound, 4-amino-N-(1-((3-chloro-2-fluoro-4-hydroxyphenyl)amino)-6-methylisoquinolin-5-yl)thieno[3,2-d]pyrimidine-7-carboxamide having inhibitory activity for protein kinases, can effectively inhibit various protein kinases including RAF, and thus can be used, singly or in combination, for prevention and treatment of diseases associated with aberrant cell growth which are caused by mutation or overexpression of RAS protein or overactivation of its associated protein kinases.

The invention claimed is:

1. A compound of formula (I), or a pharmaceutically acceptable salt or hydrate thereof:

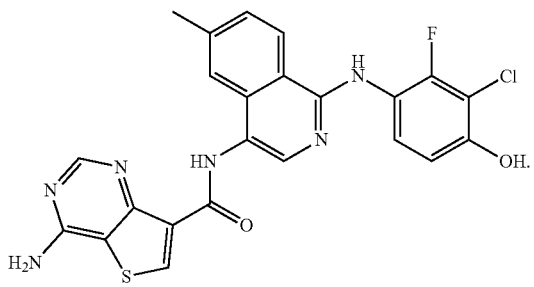

(I)

2. The compound of formula (I) of claim 1, or a pharmaceutically acceptable salt or hydrate thereof, having a purity of at least 95.0%.

3. The compound of formula (I) of claim 1, or a pharmaceutically acceptable salt or hydrate thereof, wherein said compound of formula (I), or a pharmaceutically acceptable salt or hydrate thereof, is a solid.

4. A pharmaceutical composition comprising the compound of formula (I) of claim 1, or a pharmaceutically acceptable salt or hydrate thereof, and at least one pharmaceutically acceptable excipient.

5. The pharmaceutical composition of claim 4, wherein the pharmaceutical composition further comprises a drug selected from the group consisting of: cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogens, cell differentiation/proliferation/survival inhibitors, apoptosis inhibitors, inflammation inhibitors, and P-glycoprotein inhibitors.

6. The pharmaceutical composition of claim 5 wherein the drug is a cell signal transduction inhibitor.

7. The pharmaceutical composition of claim 6 wherein the cell signal transduction inhibitor is a MEK inhibitor.

8. The pharmaceutical composition of claim 4, wherein said pharmaceutical composition is an oral composition.

9. The pharmaceutical composition of claim 4, wherein said pharmaceutical composition is in the form of a tablet, a pill, powder, a capsule, syrup, an emulsion or a microemulsion.

* * * * *